US006469228B2

(12) United States Patent
Savakis et al.

(10) Patent No.: US 6,469,228 B2
(45) Date of Patent: *Oct. 22, 2002

(54) EUKARYOTIC TRANSPOSABLE ELEMENT

(75) Inventors: Charalambos Savakis, Heraklion (GR); Gerald H. Franz, Baden (AT); Athanasios Loukeris, Athens (GR)

(73) Assignee: Minos Biosystems, Cheshire (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 63 days.

(21) Appl. No.: 08/239,765

(22) Filed: May 9, 1994

(65) Prior Publication Data

US 2002/0026650 A1 Feb. 28, 2002

Related U.S. Application Data

(62) Division of application No. 07/946,237, filed on Sep. 14, 1992, now Pat. No. 5,348,874.

(51) Int. Cl.⁷ ........................ A01K 67/033; C12N 15/00
(52) U.S. Cl. ............................................ 800/13; 800/25
(58) Field of Search ................................ 800/2, 13, 25

(56) References Cited

PUBLICATIONS

Minos–2 DNA sequence submitted to EMBL data library by Charalambos Savakis, Accession No. x61695. Released by EMBL data library on Sep. 12, 1991.*

Franz, Gerald and Savakis, Charalambos "Minos, a new transposable element from *Drosophila hydei*, is a member of the TC1–like family of transposons" Nucleic Acid Research 19 (23): 6646, 19991.*
Ashburner M. (Drosophia, a Laboratory Handbook, CSH, 1989) pp. 1049, 1051 only.
Crampton J. M. (Symp. R. Entomol. Soc. London, 1992, vol. Date 1991, 16th, 3–20).
Franz et al (1991) Nucleic Acids Research 19: 6646.
Savakis (1991) EMBL Accession No. X61695.
D O'Brochta et al (1996) Insect Biochemistry and Molecular Biology 26: 739–753 (abstract only).
RC Brand et al (1989) Mol Gen Genet 215: 469–477.
ST Seo et al (1990) J Econ Entomol 83: 1949–1953.
M Ashburner (1995) Science 270: 1941–1942.

* cited by examiner

*Primary Examiner*—Dave T. Nguyen
*Assistant Examiner*—Ram R. Shukla
(74) *Attorney, Agent, or Firm*—Kathleen Madden Williams; Elizabeth N. Spar; Palmer & Dodge LLP

(57) ABSTRACT

Disclosed are isolated transposable elements, or isolated DNA sequences which encode a transposase protein (or a portion of a transposase protein), The isolated transposable elements or the isolated DNA sequences being characterized by the ability to hybridize to the DNA sequence of Minos 1 under stringent hybridization conditions. The invention also relates to a purified transposase protein, or peptide fragments thereof, encoded by such DNA sequences. Such transposable are useful in methods for the stable introduction of a DNA sequence of interest into a eukaryotic cell. The sequence information disclosed herein is useful in the design of oligonucleotide primers which are useful for the isolation of related members of the Tc-1 family of transposable elements.

5 Claims, 3 Drawing Sheets

FIGURE 1A

```
  1  acgagcccaccactattaattcgaacagcatgttttttgcagtgcgcaatgtttaa           60
 61  cacactatattatcaatactactaaagataacacataccaatgcatttcgtctcaaagag      120
121  aatttattctcttcacgacgaaaaaaagtttgctctattccaacaacaacaaaaa            180
181  tatgagtaatttattcaaacgtttgcttaagagataagaaaaagtgaccactattaat         240
241  tcgaacgcggcgtaaGCTTACCTTAATCTCAAGAGAGCAAAACAAAAGCAACTAATGTA        300
                        M  S  Q  Y  S  M  Q  K  N
301  ACGGAATCATTATCTAGTTATGATCTGCAAATAATGTCACATACAGCAAAAAAAT            360
      T  G  I  I  S  S  Y  D  L  Q  I  M  S  H  T  A  K  K  I
361  TTTAGATTGCTGCAGATCAGTAGAAGTTTAGCAACGATGGTTCGTGGTAAACCTATTCT        420
      F  R  L  L  Q  I  S  R  S  L  A  T  M  V  R  G  K  P  I  S
421  AAAGAAATCAGAGTATTGATTAGGGATTATTTTAAATCTGAAAGACACTTACGGAGATA       480
      K  E  I  R  V  L  I  R  D  Y  F  K  S  G  K  T  L  T  E  I
481  AGCAAGCAATTAAATTTGCCTAAGTCGTCTGTGCATGGGGTGATACAAATTTTCAAAAAA       540
      S  K  Q  L  N  L  P  K  S  S  V  H  G  V  I  Q  I  F  K  K
541  AATGGGAATATTGAAAATAACATTGCCGAATAGAGGCCGAACATCAGCAATAACACCCCGC      600
      N  G  N  I  E  N  N  I  A  N  R  G  R  T  S  A  I  T  P  R
601  GACAAAAGACAACTGGCCAAAATTGTTAAGGCTGATCGTCGCCAATCTTTGAGAAATTTG      660
      D  K  R  Q  L  A  K  I  V  K  A  D  R  R  Q  S  L  R  N  L
```

FIGURE 1B

```
          A  S  K  W  S  Q  Q  L  A  K  L  S  S  E  S  G  R  D  K  L
 661      GCTTCTAAGTGGTCGCAGCAATTGGCAAAACTGTCAAGCGAGAGTGGACGCGACAAATTA      720

K  S  I  G  Y  G  F  Y  K
 721      AAAAGTATTGGATATGGTTTTTATAAgtatgtttgttattacctgtgcatcgtgtaccca      780

A  K  E  K  P  L  L  T  L  R  Q
 781      ataacttactcgtaatcttactcgtagGCCAAGGAAAAACCCTTGCTTACGCTTCGTCAA      840

*
          K  K  K  R  L  Q  W  A  R  E  R  M  S  W  T  Q  R  Q  W  D
 841      AAAAAGAAGCGTTTGCAATGGGCTCGGGAAAGGATGTCTTGGACTCAAAGGCAAATGGGAT      900
                                                                    A

T  I  I  F  S  D  E  A  K  F  D  V  S  V  G  D  T  R  K  R
 901      ACCATCATATTCAGCGATGAAGCTAAATTTGATGTTAGTGTCGGCGATACGAGAAAACGC      960

V  I  R  K  S  E  T  Y  H  K  D  C  L  K  R  T  T  K  F
 961      GTCATCCGTAAGAGTGAGACATACATACCATAAAAGACTGCCTTAAAAGAACAACAAAGTTT     1020

P  A  S  T  M  V  W  G  C  M  S  A  K  G  L  G  K  L  H  F
1021      CCTGCGAGCACTATGGTGTGGGGATGTATGTCTGCCAAAGGATTAGGAAAACTTCATTTC     1080

I  E  G  T  V  N  A  E  K  Y  I  N  I  L  Q  D  S  L  L  P
1081      ATTGAAGGGACAGTTAATGCTGAAAAATATATTTAATATTTTACAAGATAGTTTGTTGCCA     1140
```

FIGURE 1C

```
           S  I  P  K  L  S  D  C  G  E  F  F  Q  Q  D  G  A  S  S
           L
1141  TCAATACCAAAACTATCAGATTGCGGTGAATTCACTTTCAGCAGGACGGAGCATCATCG    1200

H  T  A  K  R  T  K  N  W  L  Q  Y  N  Q  M  E  V  L  D  W
           T
1201  CACACAGCCAAGCGAACCAAGCCAAAAAATTGGCTGCAATATAATCAAATGGAGGTTTTAGATTGG  1260

P  S  N  S  P  D  L  S  P  I  E  N  I  W  L  M  K  N  Q
1261  CCATCAAATAGTCCAGATCTAAGCCCAATTGAAAATATTTGGTGGCTAATGAAAAACCAG   1320

L  R  N  E  P  Q  R  N  I  S  D  L  K  I  K  L  Q  E  M  W
1321  CTTCGAAATGAGCCACAAAGGAATATTTCTGACTTGAAAATCAAGTTGCAAGAGATGTGG  1380

D  S  I  S  Q  E  H  C  K  N  L  L  S  S  M  P  K  R  V  K
1381  GACTCAATTTCTCAAGAGCATTGCAAAAATTTGTTAAGCTCAATGCCAAAACGAGTTAAA  1440

C  V  M  Q  A  K  G  D  V  T  Q  F
1441  TGCGTAATGCAGGCCAAGGGCGACGTTACACAATTCTAATATTAATTAAATTATTGTTTT  1500

1501  AAGTATGATAGTAAATCACAttacgcccgcgttcgaattaatagtggtcacttttctta    1560

1561  tctcttaagcaaaccgtttgaataattactcatatttttgttgttgttgaatagagc    1620

1621  aaaacttttttcgtcgtgaagagaataaaattctctttgagacgaaatgcattggta    1680

1681  tgtgttatcttagtagtattgataatagtgtgttaacattgcgcactgcaaaaaaa    1740

1741  acatgctgttcgaattaatagtggttggggctcgt   1775
```

EUKARYOTIC TRANSPOSABLE ELEMENT

RELATED APPLICATION

This application is a division of application Ser. No. 07,946,237 filed Sep. 14, 1992, now U.S. Pat. No. 5,348,874.

BACKGROUND OF THE INVENTION

The Tc1-like family of transposons and the retroviral-like transposons are unique for their wide dispersion in diverse organisms. Six members belonging to the Tc-1-like family have been characterized in nematodes, diptera and fish: Tc1 in *Caenorhabditis elegans,* TCb1 in *Caenorhabditis briggsae,* HB1 in *Drosophila melanogaster,* Uhu in *Drosophila heteroneura,* Minos in *Drosophila hydei* and Tes1 in the Pacific hagfish *Eptatetrus stouti.* All are characterized by a relative short length (1.6 to 1.8 kb), the presence of inverted terminal repeats, and significant sequence similarity in the region between the repeats.

The Minos-1 transposable element has been identified as a 1775 bp dispersed repetitive sequence inserted within the transcribed spacer in one of the repeats of *Drosophila hydei* (Franz and Savakis, *Nucl. Acids Res.* 19: 6646 (Dec. 11, 1991)). The element is characterized by 255-bp long perfect inverted repeats and the presence of two long, non-overlapping open reading frames (ORFs) on the same strand. The longest of the ORFs shows approximately 30% sequence identity with TcA, but does not begin with an ATG codon. It appears, therefore, that the cloned element represents a defective member of the Minos family, as is the case with all previously sequenced Tc1-like elements, with the possible exceptions of Tc1 and TCb1.

SUMMARY OF THE INVENTION

The invention relates to an isolated transposable element, or an isolated DNA sequence which encodes a transposase protein (or a portion of a transposase protein). The isolated transposable element or the isolated DNA sequence being characterized by the ability to hybridize to the DNA sequence of Minos 1 under stringent hybridization conditions. The invention also relates to a purified transposase protein, or peptide fragments thereof, encoded by such DNA sequences.

In another aspect, the invention relates to a method for the stable introduction of a DNA sequence of interest into a eukaryotic cell. This method involves the use of an isolated transposable element of the type described in the preceding paragraph, the isolated transposable element being modified to include the DNA sequence of interest flanked by the termini of the isolated transposable element. This modified transposable element is introduced into the eukaryotic cell in the presence of a transposase protein, or a DNA sequence encoding a transposase protein. The role of the transposase protein is to catalyze the transposition of the modified transposable element containing the DNA sequence of interest into the genomic DNA of the eukaryotic cell.

In a third aspect, the invention relates to a method for isolating members of the Tc-1 family of transposable elements from genomic DNA of a eukaryote of interest. According to this method, oligonucleotide primers are provided which are complementary to a sequence of at least about 12 consecutive nucleotides which encode amino acids which are highly conserved in aligned sequences of nematode Tc-1 family members and Minos family members. These oligonucleotide primers are used to prime amplification by the polymerase chain reaction (PCR). The amplification products are then used to isolate DNA encoding the entire Tc-1 family member from the eukaryote of interest by conventional methods.

BRIEF DESCRIPTION OF THE DRAWING

FIGS. 1A, 1B and 1C are diagrams providing the consensus sequence of elements Minos-1, Minos-2 and Minos-3 SEQ ID NO:3. The terminal inverted repeats and the intron sequence are shown in small letters. The deduced amino acid sequence of two open reading frames is shown above the nucleotide sequence. differences between the three elements are indicated above and below the nucleotide sequence. More specifically, nucleotide 896 is a G in Minos-2 and Minos-3 and an A in Minos-1. Nucleotide 1157 is a C in Minos-1 and Minos-3 and a T in Minos-2.

SEQUENCE LISTING CROSS-REFERENCE

In portions of the Specification excluding the claims, the following sequence listing cross-reference is applicable:

| SEQ ID NO: 1 | Minos-1 |
|---|---|
| SEQ ID NO: 2 | Minos-2 |
| SEQ ID NO: 3 | Minos-3 |
| SEQ ID NO: 4 | MVWGC |
| SEQ ID NO: 5 | WPSQSPDL |
| SEQ ID NO: 6 | WPSNSPDL |

DETAILED DESCRIPTION OF THE INVENTION

The invention disclosed herein is based on the initial discovery of Minos-1, an apparently defective member of the Tc-1 family of transposable elements. This 1775-bp element is characterized by perfect inverted repeats of 255-bp at each termini. The sequence encodes two non-overlapping reading frames, one of which has significant similarity with the putative transposase encoded by the transposable element Tc1 of *Caenorhabiditis elegans.* However, the Minos-1 element, because of a stop codon within the putative transposase gene, apparently cannot encode an active transposase.

In an effort to identify sequences related to the Minos-1 sequence, genomic DNA of *D. hydei* was probed with a portion of the Minos-1 sequence under stringent hybridization conditions. As discussed in detail in the Exemplification section which follows, two full-length related sequences were identified, both of which appear to encode an active transposase.

Isolated Nucleic Acids and Uses Thereof

Thus, in one aspect, the subject invention relates to an isolated transposable element which hybridizes to the DNA sequence of Minos-1 under stringent hybridization conditions. As used herein, stringent hybridization conditions are considered to be hybridization in a buffered solution of 0.9 M NaCl at 55° C. In *D. hydei* there are up to 30-copies detected which hybridize to Minos thus, it is likely that a large number of variants can be isolated using these conditions. Comparable hybridization stringency can be established at other salt concentrations and temperatures. This is accomplished, for example, by the inclusion of organic denaturants such as formamide in the hybridization buffer. DNA sequences which hybridize to the Minos-1 sequence under stringent hybridization conditions are referred to herein as members of the Minos family of transposable elements.

The term transposable element, as used herein, refers to a DNA sequence whose excision from/insertion into genomic DNA is catalyzed by a functional transposase protein encoded by a non-defective member of the Minos family of transposable elements. A member of the Minos family which encodes a functional transposase and possesses other necessary cis-acting elements (e.g., inverted terminal repeats) falls within this definition. In addition, a transposable element which encodes a defective transposase (e.g., Minos-1 itself) falls within this definition. As discussed in greater detail below, such defective transposable elements can be used in conjunction with a helper element (i.e., a member of the Minos family which encodes a functional transposase) to introduce a DNA sequence of interest into a eukaryotic cell.

The invention also relates to an isolated DNA sequence encoding a functional transposase protein, or a portion of a transposase protein, encoded by a member of the Minos family. Such a DNA sequence need not retain the ability to transpose in the presence of the encoded transposase protein. A sequence encoding a functional transposase protein can be used to prepare an expression construct which can be used to produce the transposase protein by recombinant DNA methodology. Such a recombinant protein can be overproduced in a eukaryotic (e.g., yeast) or prokaryotic host cell (e.g., *E. coli*), and subsequently purified by conventional methods.

The active transposase can be used in a variety of ways. For example, as discussed below, the transposase can be co-introduced into a eukaryotic cell with a modified transposon carrying a DNA sequence of interest to catalyze the insertion of the modified transposon into the genomic DNA of the eukaryotic cell. This is an alternative to the co-introduction of a helper construct in eukaryotic cells which do not constitutively produce the Minos transposase.

In addition, the transposase, or portions thereof, can be used to produce antibodies (monoclonal and polyclonal) reactive with the transposase protein. Methods for the production of monoclonal and polyclonal antibodies are straightforward once a purified antigen is available.

Through the isolation and DNA sequence analysis of additional members of the Minos family, refinement of the consensus sequence of FIG. 1 is possible. This refined consensus sequence can be used to predict modifications of the transposase protein which will affect the specific activity of the transposase. Such predictions are easily tested by modifying the DNA sequence of an expression construct encoding the transposase by site-directed mutagenesis to either bring the sequence into a greater degree of conformance with the consensus sequence, or a lesser degree of conformance with the consensus sequence. The affect of such changes on the activity of the transposase protein are monitored by assessing the affect of the mutation on transposition frequency catalyzed by the recombinant transposase.

Methods for the Introduction of DNA Sequences into a Cell

Transposable elements of the Minos family, and the active transposase encoded by such elements, are useful in methods for introducing a DNA sequence of interest into a eukaryotic cell. Typically, the DNA sequence of interest will be a gene which encodes a protein. Such a gene can be placed under the regulatory control of a promoter which can be induced or repressed, thereby offering a greater degree of control with respect to the level of the protein in the cell. In addition to a DNA sequence encoding a protein, any other DNA sequence can be introduced by this method including, for example, regulatory sequences.

The Minos transposable elements can be used to introduce a DNA sequence of interest into either germ line or somatic cells. The introduction of DNA into germ line cells has the significant advantage that the DNA sequence of interest will be contained in all cells of the mature organism and transmitted to progeny.

The Minos transposable element has been demonstrated to function in a species which is separated from the Minos source species by an evolutionary distance of 40 million years. This represents the first demonstration of a mobile element which can function autonomously in the germ line of eukaryotes separated by such an evolutionary distance and is likely to lead to the development of a long-sought transformation system applicable across taxonomic barriers.

However, even within the dipteran class, significant important applications for the Minos element exist. Listed below are examples of a variety of plant and animal pests, and human disease vectors which fall within the dipteran genus.

|  | Common Name |
|---|---|
| Agricultural Pests | |
| *Ceratitis capitata* | Medfly |
| *Anastrepha species* | Carribean fruit fly |
| *Dacus oleae* | Dacus |
| Animal Pests | |
| *Cochliomya hominivorax* | Screw Worm Fly |
| *Lucilia cuprina* | Sheep blowfly |
| *Simulium species* | Black fly |
| Human Disease Vectors | |
| *Anopheles species* | mosquito |
| *Aedes species* | mosquito |
| *Musca doinestica* | house fly |

Methods currently employed to control the populations of certain members of the dipteran class include the release of sterile males. An example of the utility of the germ line transformation methods of this invention includes the improvement of the existing release method. The methods of this invention can be used to improve such methods by enabling sexing schemes and for developing strains with desired characteristics (e.g., improved viability in the field), conditional lethal genes for improved safety, and visible or molecular genetic markers for monitoring. Genetic sexing, i.e. the capability of selectively killing the females (or transforming them into males) in mass-rearing facilities, is recognized as the most important need presently. Rearing and releasing only males has several advantages including lower breeding cost and the avoidance of population explosions due to inadvertent release of non-sterilized insects.

The methods are also useful for insects for which it might be desirable to introduce new traits in the genetic pool, rather than controlling the population levels. For example, the presence of several sympatric sub-species of *Anopheles gambiae,* all of which transmit malaria, makes it highly unlikely that population control with biological methods such as the sterile insect technique will work. An alternative scheme might involve spreading genes for refractoriness to parasite infection into the existing populations of Anopheles through the use of transposable elements. Population dynamics simulations indicate that this can be effected by releasing relatively small numbers of individuals carrying an autonomously transposing element.

The element may be actively transposing in other taxa (e.g. vertebrates) under the appropriate conditions thus, it will be recognized by those skilled in the art that the methods disclosed herein relating to diptera may be extended to higher eukaryotes. If the transposase is functional when expressed or otherwise introduced in vertebrate embryos or cells, it will be possible to develop transformation methods based on Minos elements for non-insect species as well.

A transposon-based method for producing transgenic animals or for stably transfecting cells in vitro has very important advantages compared to the methodology presently used. For example, stable integration of DNA into the germline of several mammals is now routinely achieved by micro-injecting linear DNA molecules into the nucleus of early embryos. Some of the animals that develop from injected embryos are mosaics for integration events and in only a fraction of these the germ line is involved. Moreover, most events consist of integration of tandem repeats of the injected DNA; single-insertion events do occur at higher frequencies relative to tandem insertions if DNA is injected at lower concentrations, but at a considerable cost in time and expense because the overall transformation frequencies drop.

Using a defined transposon-transposase system may overcome some or all of these problems. First, as in Drosophila, it may not be necessary to have to inject the DNA into the nucleus. If a mixture of transposon plus helper plasmids (or transposon plus purified transposase) is active when introduced into the cytoplasm, it may be possible to replace costly and time-consuming micro-injection with other methods, such as use of liposomes. Second, by controlling the relative transposon/transposase levels it may be possible to improve the overall efficiency, with a parallel increase of the frequency of single-insertion events.

Methods for the introduction of the Minos transposon into germ line cells of diptera are analogous to those previously used in connection with other transposable elements (see, e.g., *Drosophila. A Laboratory Handbook,* Ashburner, M., Cold Spring Harbor Laboratory Press, Cold Spring Harbor, N.Y., (1989)). Briefly, the most common approach is to employ a carrier/helper transposon system. The carrier transposon is a Minos transposon which has been modified by the insertion of a DNA sequence of interest in the region of the transposon flanked by the inverted terminal repeats. Typically, sequences relating to the transposase function are deleted in order to accommodate the DNA of interest. The helper transposon is a Minos transposable element which encodes an active transposase. The transposase catalyzes the transposition of the carrier transposon into the genomic DNA of the germ line eukaryotic cells. Typically, the helper and carrier are microinjected into the posterior pole of pre-blastoderm embryos, where the precursor cells of the germ line develop.

An alternative to the helper/carrier system involves the purification of active transposase (for example, from an *E. coli* culture transformed with a recombinant construct encoding the Minos transposase). The purified transposase can be co-injected into appropriately selected cells along with a carrier transposon to effect integration of the carrier into the recipient genome.

The compositions and methods of this invention are also useful for the introduction of a DNA sequence of interest into somatic cells. Typically this is accomplished in a manner analogous to the methods described in connection with germ line cells (e.g., helper/carrier systems are employed). Somatic cell introduction is typically carried out using cells grown in culture and DNA can be introduced, for example, by calcium co-precipitation or other conventional methods.

Methods for Isolating Additions Tc-1 Family Members

DNA sequence analysis of the members of the Minos family disclosed herein, and comparison of this sequence information to the sequences of Tc-1 family members from evolutionarily distant organisms (e.g., nematode), reveal short stretches of conserved amino acid sequence within the transposase coding region. This high degree of conservation suggests a method for isolating Tc-1 family members from diverse eukaryotic species.

This method involves the amplification of DNA by polymerase chain reaction from a eukaryote of interest using primers which are complementary complementary to a sequence of at least about 12 consecutive nucleotides which encode amino acids which are highly conserved in aligned sequences of nematode Tc-1 family members and dipteran Minos family members. Such amino acid sequences include, for example, MVWGC, WPSQSPDL and WPSNSPDL.

Exemplification

Materials and Methods

Fly strains. Standard procedures were used for culturing of *Drosophila hydei*. All strains used in this study have been used previously for rDNA work and are named for the X and Y chromosomes. Strain $bb^1$ ($bb^1/bb^1$ x $bb^1/Y$) carries a bobbed X chromosome; strain $X^7$ ($X^7/X^7 \times X^7/Y$) is a subline of the Dusseldorf wild-type strain; strain $X^{\wedge}X/Y(X^{\wedge}X/Y \times X/Y)$ females carry a compound X chromosome which has no rDNA. Strain wm1/Y (wm1/Y×X-3/Y) females have a compound X chromosome (wm1); males carry a X-autosome 3 translocation which has no rDNA.

DNA manipulations and sequencing. All basic procedures were carried out essentially as described (Maniatis et al. 1982). DNA from adult females of strain $bb^1$ was partially digested with EcoRI and cloned into phage vector λgt7. To recover new Minos elements, the library was screened by hybridization with a 1.7 kb HhaI fragment which contains most of the Minos-1 sequence. For sequencing, the appropriate restriction fragments from positive clones were subcloned into plasmid vectors pUC8 and pUC9 and nested deletions were generated by digestion with exonuclease Bal31 followed by subcloning. Sequencing was performed by conventional methods. Both strands were sequenced, with a minimum of two independent sequences for each base pair.

Sequence analysis. Database searches and sequence analysis and manipulations were performed using programs FASTA (Pearson and Lipman, *Proc. Natl. Acad. Sci. USA* 85:2444–2448 (1988)). BLAST (Altschul et al., *J. Mol. Biol.* 215:403–410 (1990)) and the computer package GCG (Devereux et al., *Nuc. Acids Res.* 12:387–395 (1984)). The program CLUSTAL (Higgins and Sharp, 1988) was used for protein sequence alignments.

Results

The sequence of Minos. Three new representatives of the Minos family of transposable elements have been cloned and sequenced; they have been named Minos-2, Minos-3 and Minos-4, Minos-1 being the element reported previously. Minos-2 and Minos-3 are complete elements distinct from Minos-1, as judged from the restriction maps of the flanking DNA and the flanking sequences. The sequences of the elements, summarized in FIG. 1, show very little variation, differing in only two positions. At position 896 of the sequence, Minos-2 and Minos-3 have a G instead of the A found in Minos-1. This transition changes a TAG stop codon to TGG and restores a 603 bp ORF beginning with ATG at position 874. The second difference is at nucleotide 1157, which is a C in Minos-1 and Minos-3 and a T in Minos-2. This causes a ser→leu substitution in ORF2 of Minos-2, relative to Minos-1 and Minos-3. Minos-2 and 3, therefore, have two complete ORFs beginning with an ATG; ORF1, which can encode a 138 amino-acid peptide, and ORF2, which can encode a 201 amino-acid peptide.

The Minos-4 clone does not contain a complete element. The sequence of the cloned DNA fragment begins at the EcoRI site found at position 1168 of the other members and is identical to the Minos-1 sequence to base 1775. Apparently Minos-4 represents a partial isolate rather than a defective member of the family, since the library from which it was isolated was from DNA cut with EcoRI.

The DNA sequence flanking the cloned elements are different from each other; this indicates that these elements are inserted at different sites of the *D. hydei* genome, and are, therefore, distinct. These sequences are mainly characterized by a high A/T content, and do not show any other obvious similarity. In all cases, the inverted repeats end with the dinucleotide TA, which is at the same time a direct and an inverted repeat. Because of this, there is some ambiguity in defining the ends of the element precisely. Shown below are the sequences of the Minos 1–4 insertions sites. The rDNA sequences flanking the Minos elements are shown in lower case and Minos sequences are shown in upper case. The rDNA sequence identical to the flanking DNA of Minos-1 has been aligned with the Minos-1 insertion sequence. It is noted that since gapped sequences are treated as separate sequences for purposes of the Rules of Practice in Patent Cases (37 CFR 1.822(o)), and since each of the separate sequences contain less than 10 nucleotides, the sequences shown below have not been listed in the Sequence Listing.

In the case of Minos-1, which is inserted into a region which has been previously sequenced, the external transcribed spacer of the rDNA repeat, there are two possibilities. As shown below, deleting the sequence which begins with ACGA and end with TCGT would restore the rDNA sequence; the element, with an A and a T at the two ends may have inserted between a T and an A. In this possibility, the element would be 1775 bp long with 255 bp inverted repeats. Alternatively, the element may begin and end with CGA . . . TCG and produce a target site duplication, as happens with many other mobile elements. In this possibility the target site duplication would involve the dinucleotide TA, and the size of the element would be 1773 bp. For numbering, the A of the TA repeat has been designated nucleotide number 1 of the Minos-1–3 sequences.

| rDNA | ataat--------------------attaa |
|---|---|
| Minos-1 | ataatACGA------------TCGTattaa |
| Minos-2 | aatatACGA------------TCGTataat |
| Minos-3 | gctttACGA------------TCGTagaag |
| Minos-4 | tttctACGA |
| | 1775                                    1 |

Mobility and homogeneity of Minos elements. The striking degree of sequence conservation among the cloned Minos elements suggests that, as in the case of Tc1, all Minos elements may be highly homogeneous. To test this the single HhaI site within each of the terminal repeats of Minos was exploited. The 1.68 kB HhaI fragment of Minos-1 was used as probe in a Southern blot of genomic DNA from the same strains, digested with CfoI, an isoschisomer of HhaI. A single, strong band of approximately 1.7 kb was detectable in all lanes, indicating that no major deletions or rearrangements are present in the Minos elements present in these strains.

Comparison of the proteins encoded by Tc1 and Minos. The deduced 201 amino acid sequence of the ORF2 in Minos-2 and Minos-3 shows significant sequence similarity with the 201 carboxy terminal residues of TcA, the putative transposase of Tc1; alignment of the sequences gives 63 identities (31%) and 91 conservative substitutions (45%) with only two single-residue insertion-deletions. The two sequences, however, differ in size; TcA has 72 additional amino acids at the amino end. The 50 amino-terminal residues of TcA show weak but significant sequence similarity with the carboxy terminus of Minos ORF2; introduction of a 60-bp deletion in the Minos DNA sequence creates a long open reading frame which contains most of ORF1 (codons 1 to 138) and the entire ORF2 extended by 22 codons upstream of the ATG. Interestingly, this 60-bp sequence, from base 748 to base 807 of the Minos sequence, exhibits features of an intron. More specifically, the 5' and 3' ends conform to the consensus splice donor and acceptor sites and a version of the internal splice signal consensus is found 30 nucleotides upstream from the 3' end.

Divergence of the TcA-related sequences. Although Minos inhabits a Drosophila species, it is not more related to the other Tc1-like elements from Drosophila species, HB1 and Uhu. These elements, or at least the members which have been sequenced, do not contain open reading frames comparable in length to that of Tc1. However, if small numbers of deletions and insertions are introduced in their DNA sequences, open reading frames can be generated which show significantly similarity with the TcA sequence. Most of these insertion-deletion changes involve one nucleotide, presumably representing mutations which have accumulated in these inactive elements. Table 1 shows a similarity matrix between the three Drosophila and the two nematode elements, in the regions corresponding to the hypothetical Minos exon 2. In Table 1, percent identities are shown above the diagonal; identical/total positions are shown below the diagonal. Minos shows approximately the same degree of similarity (between 28 and 36 percent identity) with all the other elements; HB1 and Uhu show comparable similarities. In a multiple sequence alignment of the same regions, 21 of the resulting 225 positions (9%) are invariant and 49 positions (22%) are occupied by related amino acids. It should also be noted that the similarity between HB1 and Uhu with Tc1 and Minos extends another 18 codons upstream from the position corresponding to the first codon of the hypothetical exon 2 of Minos. No other significant similarities can be detected between Tc1, Uhu, HB1 and Minos in the sequences between the terminal repeats.

TABLE 1

|  | Tc1 | TCb1 | Minos | Uhu | HB1 |
|---|---|---|---|---|---|
| Tc1 |  | 71 | 31 | 44 | 33 |
| TCb1 | 160/223 |  | 34 | 41 | 35 |
| Minos | 70/221 | 75/222 |  | 36 | 28 |
| Uhu | 96/217 | 89/217 | 78/218 |  | 31 |
| HB1 | 73/223 | 79/223 | 62/222 | 68/219 |  |

The ORF1 sequence is related to the paired box sequence. The 88-residue amino terminal sequence of Minos ORF1 shows no apparent similarity with any Tc1 sequences. Searches of the nucleic acid and protein sequence data libraries with the sequence using the FASTA and WORD-SEARCH algorithms gave no significant matches. However, the Basic Local Alignment Search Tool program revealed a similarity with the paired box sequence, a peptide sequence found in the Drosophila paired gene product, and conserved in other Drosophila and mammalian genes. This similarity extends approximately between residues 19 to 115 of the Minos sequence, and residues 35 to 131 of the Drosophila paired protein. Alignment of the Minos sequence with the Drosophila and human paired box sequences for maximum similarity shows 16 invariant positions in this region (17%) and 49 positions occupied by related amino acids (51%). The corresponding values for the human and Drosophila paired sequences are 72% identities and 23% conserved positions.

Although the Minos-paired similarity is weak compared to that between the Drosophila and human paired sequences, it is statistically significant. The similarity scores between the Minos sequence (amino acids 1 to 118 of ORF1) to the corresponding human paired sequence (amino acids 17 to 135 of the published sequence) is approximately 10 standard deviations higher than the average of the scores obtained from 50 comparisons made between the Minos sequence and 50 randomly shuffled human paired sequences.

Transposition in D. melanogaster. A D. melanogaster "helper" strain which can overproduce the Minos transposase upon exposure to heat shock was constructed. The strain was constructed by introducing a modified Minos element into the germ line by conventional P element transformation (see, e.g., Drosophila. A Laboratory Handbook, Ashburner, M., Cold Spring Harbor Laboratory Press, Cold Spring Harbor, N.Y., (1989)). To place the Minos transposase under heat shock control, the left-hand terminal repeat of Minos-2 was replaced by the D. melanogaster hsp 70 promoter. This modified element was inserted into the P element transformation vector pDM30, which contains a wild-type copy of the Drosophila rosy (ry) gene as a dominant visible marker. The plasmid (pPhsM2) was injected into pre-blastoderm embryos of a ry strain, injected GO adults were mated to ry flies and $ry^+$ G1 progeny were bred further. Three independent transformants were recovered, two on the third chromosome (named M46 and M67) and one on the X (M84). Southern blots using ry and Minos probes indicated that each of the three transformants contains a single insertion of the complete sequence between the P element ends. Northern blots of total RNA from adult transformed flies subjected to a heat shock showed abundant transcripts hybridizing to Minos probes. No Minos-related transcripts have been detected by the same probes in RNA from non-heat shocked flies. The structure of the RNA transcripts was investigated in another series of experiments discussed below.

Breeding of these transformants showed that they are all homozygous lethal. This observation was unexpected; the recovery of recessive lethal mutations due to insertional inactivation of essential genes is a rather uncommon event in P transformation experiments. Moreover, the insertion into the X clearly has not caused a "knock-out" mutation since hemizygous males are viable and fertile; only homozygous females are inviable. This behavior suggested that the lethality may be dosage- or pairing-dependent; the latter being more likely because double heterozygotes of the two insertions in the 3rd chromosome are viable. The observed lethality is a useful feature which enables one to follow the segregation of the "helper" chromosomes by keeping them over genetically marked balancers.

Strong evidence for Minos transposition in the germ line was obtained by first introducing the M67 chromosome into a white background (y,w; TM3/M67). Pre-blastoderm embryos were injected with a plasmid (pM2w) containing a complete Minos-2 element with a wild-type copy of the white (w) gene inserted into its unique EcoRI restriction site within ORF2. The inserted w sequences provide a dominant selectable marker; in addition they interrupt ORF2, making the production of active transposase from this construct highly improbable. Three separate experiments were conducted: in experiment A injected embryos and the developing larvae and adults were kept at 18° C., in experiment B they were kept at 25° C. throughout development, and in experiment C the embryos were subjected to a 1-hour 37° C. heat shock three hours after injection. All emerging GO flies (63, 38 and 61, from experiments A, B and C, respectively) were mated to y,w; TM3/Dgl3 flies and the progeny were scored for the appearance of the $w^+$ phenotype. To date, at least four independent germ line transformation events have been detected in experiments A and B. Two of these events come from a single GO male from experiment A and at least two have been recovered from two different GO flies from experiment B. The results are shown in Table 2 below:

TABLE 2

| Experiment | GO | #G1 Scored | $w^+$ G1 | Insertion Chromosome |
|---|---|---|---|---|
| A | A10 | 286 | A10.1 | X |
|  |  |  | A10.2 | 3 |
|  |  |  | A10.3 | 3 |
|  |  |  | A10.4 | ? |
|  |  |  | A10.5 | ? |
|  |  |  | A10.6 | ? |
| B | B13 | 75 | B13.1-3 | ? |
| C | B33 | 116 | B33.1-18 | ? |

Evidence that the Minos-$w^+$ transposon can be mobilized in the soma of flies which produce the transposase has been obtained. Larvae of the constitution y,w; TM3/[M2w]M67 (progeny of the A10.2 fly), which contain both transposon and helper sequences, were subjected to heat shock and adult flies were examined for the appearance of eye color mosaicism. More than 50% of the flies showed mosaicism of different degrees. Patches of ommatidia with either reduced or increased pigmentation were observed which is consistent with the expected result of a somatic deletion or transposition event. No mosaicism has been detected in flies not subjected to a heat shock at the larval stage. The somatic instability results clearly indicate that the $w^+$ insertions are minos-mediated.

Analysis of Minos mRNA Transcripts. Total RNA was isolated from the M67 strain, the construction of which is described above. The structure of mRNA transcripts was investigated by the polymerase chain reaction (PCR) method of DNA amplification. A particularly important aspect of this investigation was to determine the status of the 60 base pair putative intron region (discussed above) in the mRNA transcripts. As was mentioned previously, this sequence is characterized by 5' and 3' ends which conform to the consensus splice donor and acceptor sites, and has a version of the internal splice signal consensus sequence 30 nucleotides upstream from the 3' end.

To determine the status of this putative intron, PCR priming sites were selected from exon sequences (ORF1 and ORF2) flanking the putative intron. The PCR product synthesized in this reaction was cloned and sequenced by conventional methods. The sequencing experiments revealed unambiguously that the 60 base pair intron sequence was, in fact, absent in the amplified DNA.

The removal of the 60-bp sequence in the correctly spliced primary transcript initiating upstream from ORF1, results in the generation of a 1083-bp open reading frame which encodes a peptide of 361 amino acids. An alignment of the 273 carboxy-terminal amino acids of this peptide with the sequences of TcA and the 273-residue hypothetical peptide of TCb1 was generated by the multiple alignment program CLUSTAL, which introduces gaps in the sequences to achieve maximum sequence similarity. The three sequences were aligned without the need of any insertions-deletions (with the exception of the two one-residue gaps required for optimal alignment in the ORF2 region) and show an overall 28% identity, i.e. 76 of the 273 positions are invariant. In the region upstream from the first methionine of ORF2, twelve out of seventy two positions (16%) are invariant; 29 positions (40%) are occupied by structurally related amino acid residues. Although this degree of similarity is lower than that in the ORF2 region, it is statistically significant.

The sequence similarity between TcA and the carboxy end of the Minos hypothetical protein is also reflected in their secondary structures. Comparisons of α-helix and β-sheet predictions and hydrophobicity profiles between the Tc1 and Minos sequence show similarities in several regions. Another feature of the sequences is their high content, approximately 20%, in basic amino acids. TcA has 29 arginines, 16 lysines and 11 histidines, and the TcA-related Minos sequence has 20 arginines, 32 lysines and 4 histidines. These are more abundant at the amino-terminal half of both sequences, although the position of most is not strictly conserved. The proteins are fairly basic, with computed isoelectric points of 11.27 for TcA and 10.73 for the related Minos peptide. The computed pI of the complete hypothetical 361 amino acid Minos protein is 10.97.

Equivalents

Those skilled in the art will recognize or be able to ascertain, using no more than routine experimentation, many equivalents to the specific embodiments of the invention described herein. Such equivalents are intended to be encompassed by the following claims.

What is claimed is:

1. A transgenic dipteran comprising a heterologous DNA of interest integrated into genomic DNA of said transgenic dipteran, wherein said transgenic dipteran is produced by a method comprising:
   a) providing an isolated transposable element comprising a first DNA sequence which hybridizes to the DNA sequence of SEQ ID NO: 1 under stringent hybridization conditions, the isolated transposable element being modified to include the heterologous DNA of interest flanked by the inverted terminal repeats of the isolated transposable element;
   b) introducing the modified transposable element of step a) into a dipteran germ line cell, wherein the germ line cell comprises:
      (i) a transposase protein encoded by said first DNA sequence of step a), wherein said first DNA sequence is selected from the group consisting of SEQ ID NO: 2 and SEQ ID NO: 3; or
      (ii) an expression vector comprising the first DNA sequence of step a) encoding said transposase protein;
   c) allowing the germ line cell to develop into a dipteran;
   d) mating the dipteran of step c) to obtain a progeny; and
   e) screening said progeny for the expression of the heterologous DNA of interest, wherein the heterologous DNA of interest is a genetic marker or is expressed to confer a visible phenotype.

2. The transgenic dipteran of claim 1 wherein the heterologous DNA of interest provides a molecular genetic marker or expression of the heterologous DNA of interest confers a visible phenotype.

3. Progeny of the transgenic dipteran of claim 1, wherein said progeny contains in its germ line the heterologous DNA of interest.

4. A transgenic dipteran comprising a heterologous DNA of interest integrated into genomic DNA of said transgenic dipteran, wherein said transgenic dipteran is produced by a method comprising:
   a) providing an isolated transposable element comprising a first DNA sequence which hybridizes to the DNA sequence of SEQ ID NO: 1 under stringent hybridization conditions, the isolated transposable element being modified to include the heterologous DNA of interest flanked by the inverted terminal repeats of the isolated transposable element;
   b) introducing the modified transposable element of step a) into a dipteran germ line cell, wherein the germ cell line is of Ceratitis capitata, and wherein the germ line cell comprises:
      (i) a transposase protein encoded by said first DNA sequence of step a), wherein said first DNA sequence is selected from the group consisting of SEQ ID NO: 2 and SEQ ID NO: 3; or
      (ii) an expression vector comprising the first DNA sequence of step a) encoding said transposase protein;
   c) allowing the germ line cell to develop into a dipteran;
   d) mating the dipteran of step c) to obtain a progeny; and
   e) screening said progeny for the expression of the heterologous DNA of interest, wherein the heterologous DNA of interest is a genetic marker or is expressed to confer a visible phenotype.

5. Progeny of the transgenic dipteran of claim 4, wherein said progeny contains in its germ line the heterologous DNA of interest.

* * * * *

SEQUENCE LISTING

```
<160> NUMBER OF SEQ ID NOS: 6

<210> SEQ ID NO 1
<211> LENGTH: 1775
<212> TYPE: DNA
<213> ORGANISM: Drosophila hydei

<400> SEQUENCE: 1
acgagcccca accactatta attcgaacag catgttttt  ttgcagtgcg caatgtttaa      60
cacactatat tatcaatact actaaagata acacatacca atgcatttcg tctcaaagag     120
aattttattc tcttcacgac gaaaaaaaaa gttttgctct atttccaaca acaacaaaaa     180
tatgagtaat ttattcaaac ggtttgctta agagataaga aaaagtgac cactattaat      240 tcgaacgcgg cgtaagctta ccttaatctc aagaagagca aaacaaaagc aactaatgta     300
acggaatcat tatctagtta tgatctgcaa ataatgtcac aatacagcat gcaaaaaat     360 tttagattgc tgcagatcag tagaagttta gcaacgatgg ttcgtggtaa acctatttct     420
aaagaaatca gagtattgat tagggattat tttaaatctg gaaagacact tacggagata     480
agcaagcaat taaatttgcc taagtcgtct gtgcatgggg tgatacaaat tttcaaaaaa     540
aatgggaata ttgaaaataa cattgcgaat agaggccgaa catcagcaat aacaccccgc     600
gacaaaagac aactggccaa aattgttaag gctgatcgtc gccaatcttt gagaaatttg     660
gcttctaagt ggtcgcagca attggcaaaa ctgtcaagcg agagtggacg cgacaaatta     720
aaaagtattg gatatggttt ttataaagta tgttttgtta ttacctgtgc atcgtaccca     780
ataacttact cgtaatctta ctcgtaggcc aaggaaaaac ccttgcttac gcttcgtcaa     840
aaaaagaagc gtttgcaatg ggctcgggaa aggatgtctt ggactcaaag gcaataggat     900
accatcatat tcagcgatga agctaaattt gatgttagtg tcggcgatac gagaaaacgc     960
gtcatccgta agaggtcaga aacataccat aaagactgcc ttaaaagaac aacaaagttt    1020
cctgcgagca ctatggtatg gggatgtatg tctgccaaag gattaggaaa acttcatttc    1080
attgaaggga cagttaatgc tgaaaaatat attaatattt tacaagatag tttgttgcca    1140
tcaataccaa aactatcaga ttgcggtgaa ttcacttttc agcaggacgg agcatcatcg    1200
cacacagcca agcgaaccaa aaattggctg caatataatc aaatggaggt tttagattgg    1260
ccatcaaata gtccagatct aagcccaatt gaaaatattt ggtggctaat gaaaaaccag    1320
cttcgaaatg agccacaaag gaatatttct gacttgaaaa tcaagttgca agagatgtgg    1380
```

```
gactcaattt ctcaagagca ttgcaaaaat ttgttaagct caatgccaaa acgagttaaa    1440
tgcgtaatgc aggccaaggg cgacgttaca caattctaat attaattaaa ttattgtttt    1500
aagtatgata gtaaatcaca ttacgccgcg ttcgaattaa tagtggtcac ttttttctta    1560
tctcttaagc aaaccgtttg aataaattac tcatatttt gttgttgttg gaaatagagc     1620 aaaactttt ttttcgtcgt gaagagaata aaattctctt tgagacgaaa tgcattggta     1680
tgtgttatct ttagtagtat tgataatata gtgtgttaaa cattgcgcac tgcaaaaaaa    1740
acatgctgtt cgaattaata gtggttgggg ctcgt                               1775
```

<210> SEQ ID NO 2
<211> LENGTH: 1775
<212> TYPE: DNA
<213> ORGANISM: Drosophila hydei

<400> SEQUENCE: 2

```
acgagcccca accactatta attcgaacag catgttttt ttgcagtgcg caatgtttaa     60
cacactatat tatcaatact actaaagata acacatacca atgcatttcg tctcaaagag    120
aattttattc tcttcacgac gaaaaaaaaa gttttgctct atttccaaca acaacaaaaa    180
tatgagtaat ttattcaaac ggtttgctta agagataaga aaaagtgac cactattaat     240 tcgaacgcgg cgtaagctta ccttaatctc aagaagagca aacaaaagc aactaatgta     300 acggaatcat tatctagtta tgatctgcaa ataatgtcac aatacagcat gcaaaaaat     360 tttagattgc tgcagatcag tagaagttta gcaacgatgg ttcgtggtaa acctatttct    420
aaagaaatca gagtattgat tagggattat tttaaatctg gaaagacact tacggagata    480
agcaagcaat taaatttgcc taagtcgtct gtgcatgggg tgatacaaat tttcaaaaaa    540
aatgggaata ttgaaaataa cattgcgaat agaggccgaa catcagcaat aacaccccgc    600
gacaaaagac aactggccaa aattgttaag gctgatcgtc gccaatcttt gagaaatttg    660
gcttctaagt ggtcgcagca attggcaaaa ctgtcaagcg agagtggacg cgacaaatta    720
aaaagtattg gatatggttt ttataaagta tgttttgtta ttacctgtgc atcgtaccca    780
ataacttact cgtaatctta ctcgtaggcc aaggaaaaac ccttgcttac gcttcgtcaa    840
aaaaagaagc gttttgcaatg ggctcgggaa aggatgtctt ggactcaaag gcaatgggat   900
accatcatat tcagcgatga agctaaattt gatgttagtg tcggcgatac gagaaaacgc    960
gtcatccgta agaggtcaga aacataccat aaagactgcc ttaaagaac aacaaagttt     1020 cctgcgagca ctatggtatg gggatgtatg tctgccaaag gattaggaaa acttcatttc    1080
attgaaggga cagttaatgc tgaaaaatat attaatattt tacaagatag tttgttgcca    1140
tcaataccaa aactattaga ttgcggtgaa ttcactttc agcaggacgg agcatcatcg     1200
cacacagcca agcgaaccaa aaattggctg caatataatc aaatggaggt tttagattgg    1260
ccatcaaata gtccagatct aagcccaatt gaaaatattt ggtggctaat gaaaaaccag    1320
cttcgaaatg agccacaaag gaatatttct gacttgaaaa tcaagttgca agagatgtgg    1380
gactcaattt ctcaagagca ttgcaaaaat ttgttaagct caatgccaaa acgagttaaa    1440
tgcgtaatgc aggccaaggg cgacgttaca caattctaat attaattaaa ttattgtttt    1500
aagtatgata gtaaatcaca ttacgccgcg ttcgaattaa tagtggtcac ttttttctta    1560
tctcttaagc aaaccgtttg aataaattac tcatatttt gttgttgttg gaaatagagc     1620 aaaactttt ttttcgtcgt gaagagaata aaattctctt tgagacgaaa tgcattggta     1680
```

-continued

```
tgtgttatct ttagtagtat tgataatata gtgtgttaaa cattgcgcac tgcaaaaaaa    1740
acatgctgtt cgaattaata gtggttgggg ctcgt                                1775

<210> SEQ ID NO 3
<211> LENGTH: 1775
<212> TYPE: DNA
<213> ORGANISM: Drosophila hydei

<400> SEQUENCE: 3
acgagcccca accactatta attcgaacag catgtttttt ttgcagtgcg caatgtttaa      60
cacactatat tatcaatact actaaagata acacatacca atgcatttcg tctcaaagag     120
aattttattc tcttcacgac gaaaaaaaaa gttttgctct atttccaaca acaacaaaaa     180
tatgagtaat ttattcaaac ggtttgctta agagataaga aaaagtgac cactattaat      240 tcgaacgcgg cgtaagctta ccttaatctc aagaagagca aaacaaaagc aactaatgta     300
acggaatcat tatctagtta tgatctgcaa ataatgtcac aatacagcat gcaaaaaaat     360
tttagattgc tgcagatcag tagaagttta gcaacgatgg ttcgtggtaa acctatttct     420
aaagaaatca gagtattgat tagggattat tttaaatctg gaaagacact tacggagata     480
agcaagcaat taaatttgcc taagtcgtct gtgcatgggg tgatacaaat tttcaaaaaa     540
aatgggaata ttgaaaataa cattgcgaat agaggccgaa catcagcaat aacaccccgc     600
gacaaaagac aactggccaa aattgttaag gctgatcgtc gccaatcttt gagaaatttg     660
gcttctaagt ggtcgcagca attggcaaaa ctgtcaagcg agagtggacg cgacaaatta     720
aaaagtattg gatatggttt ttataaagta tgttttgtta ttacctgtgc atcgtaccca     780
ataacttact cgtaatctta ctcgtaggcc aaggaaaaac ccttgcttac gcttcgtcaa     840
aaaaagaagc gtttgcaatg ggctcgggaa aggatgtctt ggactcaaag gcaatgggat     900
accatcatat tcagcgatga agctaaattt gatgttagtg tcggcgatac gagaaaacgc     960
gtcatccgta agaggtcaga aacataccat aaagactgcc ttaaaagaac aacaaagttt    1020
cctgcgagca ctatggtatg gggatgtatg tctgccaaag gattaggaaa acttcatttc    1080
attgaaggga cagttaatgc tgaaaaatat attaatattt tacaagatag tttgttgcca    1140
tcaataccaa aactatcaga ttgcggtgaa ttcactttc agcaggacgg agcatcatcg     1200
cacacagcca agcgaaccaa aaattggctg caatataatc aaatggaggt tttagattgg    1260
ccatcaaata gtccagatct aagcccaatt gaaaatattt ggtggctaat gaaaaaccag    1320
cttcgaaatg agccacaaag gaatatttct gacttgaaaa tcaagttgca agagatgtgg    1380
gactcaattt ctcaagagca ttgcaaaaat ttgttaagct caatgccaaa acgagttaaa    1440
tgcgtaatgc aggccaaggg cgacgttaca caattctaat attaattaaa ttattgtttt    1500
aagtatgata gtaaatcaca ttacgccgcg ttcgaattaa tagtggtcac tttttttctta    1560 tctcttaagc aaaccgtttg aataaattac tcatattttt gttgttgttg gaaatagagc    1620 aaaactttt ttttcgtcgt gaagagaata aaattctctt tgagacgaaa tgcattggta    1680
tgtgttatct ttagtagtat tgataatata gtgtgttaaa cattgcgcac tgcaaaaaaa    1740
acatgctgtt cgaattaata gtggttgggg ctcgt                                1775

<210> SEQ ID NO 4
<211> LENGTH: 5
<212> TYPE: PRT
<213> ORGANISM: Unknown
<220> FEATURE:
<223> OTHER INFORMATION: Conserved amino acid sequence of the TC-1
```

-continued

```
        family of transposable elements

<400> SEQUENCE: 4

Met Val Trp Gly Cys
1               5

<210> SEQ ID NO 5
<211> LENGTH: 8
<212> TYPE: PRT
<213> ORGANISM: Unknown
<220> FEATURE:
<223> OTHER INFORMATION: Conserved amino acid sequence of the TC-1
      family of transposable elements

<400> SEQUENCE: 5

Trp Pro Ser Gln Ser Pro Asp Leu
1               5

<210> SEQ ID NO 6
<211> LENGTH: 8
<212> TYPE: PRT
<213> ORGANISM: Unknown
<220> FEATURE:
<223> OTHER INFORMATION: Conserved amino acid sequence of the TC-1
      family of transposable elements

<400> SEQUENCE: 6

Trp Pro Ser Asn Ser Pro Asp Leu
1               5
```